US010716816B2

(12) United States Patent
Kyle et al.

(10) Patent No.: US 10,716,816 B2
(45) Date of Patent: Jul. 21, 2020

(54) ACTIVATED BIFIDOBACTERIA AND METHODS OF USE THEREOF

(71) Applicant: EVOLVE BIOSYSTEMS INC., Davis, CA (US)

(72) Inventors: David Kyle, Gualala, CA (US); David Mills, Davis, CA (US); Samara Freeman-Sharkey, Davis, CA (US)

(73) Assignee: EVOLVE BIOSYSTEMS INC., Davis, CA (US)

( * ) Notice: Subject to any disclaimer, the term of this patent is extended or adjusted under 35 U.S.C. 154(b) by 0 days.

(21) Appl. No.: 15/521,502

(22) PCT Filed: Oct. 23, 2015

(86) PCT No.: PCT/US2015/057226
§ 371 (c)(1),
(2) Date: Apr. 24, 2017

(87) PCT Pub. No.: WO2016/065324
PCT Pub. Date: Apr. 28, 2016

(65) Prior Publication Data
US 2017/0304375 A1    Oct. 26, 2017

Related U.S. Application Data

(60) Provisional application No. 62/133,243, filed on Mar. 13, 2015, provisional application No. 62/068,553, filed on Oct. 24, 2014.

(51) Int. Cl.
*A61K 35/745* (2015.01)
*A23L 29/30* (2016.01)
(Continued)

(52) U.S. Cl.
CPC .............. *A61K 35/745* (2013.01); *A23C 9/12* (2013.01); *A23L 29/30* (2016.08); *A23L 33/135* (2016.08);
(Continued)

(58) Field of Classification Search
None
See application file for complete search history.

(56) References Cited

U.S. PATENT DOCUMENTS

| 5,716,615 A | 2/1998 | Cavaliere Vesely et al. |
| 9,579,353 B2 | 2/2017 | Olmstead |

(Continued)

FOREIGN PATENT DOCUMENTS

| RU | 2180915 C1 | 3/2002 |
| UA | 32462 U | 5/2008 |

(Continued)

OTHER PUBLICATIONS

Navabi et al. "Gastrointestinal Cell Lines Form Polarized Epithelia with an Adherent Mucus Layer with Cultured . . . " PLOS One Jul. 2013 vol. 8 Issue 7 pp. 1-15 (Year: 2013).*

(Continued)

*Primary Examiner* — Felicia C Turner
(74) *Attorney, Agent, or Firm* — Arent Fox LLP

(57) ABSTRACT

Some embodiments of the invention include a composition and method for treating dysbiosis in infants. The composition may include a mixture of activated bifidobacteria and a complex oligosaccharide wherein the complex oligosaccharide may be derived from a human or non-human source.

22 Claims, 2 Drawing Sheets

(51) Int. Cl.
| | |
|---|---|
| C12N 1/04 | (2006.01) |
| C12N 1/20 | (2006.01) |
| A61K 31/702 | (2006.01) |
| A23L 33/135 | (2016.01) |
| A23C 9/12 | (2006.01) |

(52) U.S. Cl.
CPC .............. *A61K 31/702* (2013.01); *C12N 1/04* (2013.01); *C12N 1/20* (2013.01); *A23V 2002/00* (2013.01); *A23Y 2300/45* (2013.01)

(56) References Cited

U.S. PATENT DOCUMENTS

| | | | |
|---|---|---|---|
| 9,649,380 B2 | 5/2017 | Longoni et al. | |
| 2007/0082087 A1* | 4/2007 | Kuo .................... | A23C 9/1234 426/43 |
| 2009/0253790 A1* | 10/2009 | Smith .................... | A23C 3/08 514/557 |
| 2010/0113383 A1 | 5/2010 | Mills et al. | |
| 2010/0183559 A1 | 7/2010 | Van Sinderren et al. | |
| 2010/0260720 A1 | 10/2010 | Sprenger | |
| 2011/0064707 A1 | 3/2011 | Rochat et al. | |
| 2011/0110904 A1 | 5/2011 | Fichot et al. | |
| 2011/0165127 A1 | 7/2011 | Masri | |
| 2013/0195803 A1 | 8/2013 | German et al. | |

FOREIGN PATENT DOCUMENTS

| | | | | |
|---|---|---|---|---|
| WO | 2007046697 A1 | | 4/2007 | |
| WO | 2013123223 | | 8/2013 | |
| WO | WO 2013/123223 | * | 8/2013 | ............... C07K 7/06 |
| WO | 2016065324 A1 | | 4/2016 | |
| WO | 2016094836 A1 | | 6/2016 | |

OTHER PUBLICATIONS

Gonzalez-Rodriguez "Factors involved in the colonization and survival of Bifidobacteria . . . " FEMS Microbiology Letters vol. 349 pp. 1-10 (Year: 2013).*

International Search Report and Written Opinion for PCT/US2015/057226 dated Jan. 8, 2016.

Chichlowski, Ph.D., Maciej et al., "Bifidobacteria isolated from infants and cultured on human milk oligosaccharides affect intestinal epithelial function," Journal of Pediatric Gastroenterology and Nutrition (Sep. 2012) vol. 55, No. 3, pp. 321-327.

Kavanaugh, Devon W. et al., "Exposure of *Bifidobacterium longum* subsp. *infantis* to Milk Oligosaccharides Increases Adhesion to Epithelial Cells and Induces a Sustantial Transcriptional Response," PLos ONE (Jun. 2013) vol. 8, No. 6 e67224, pp. 1-4.

LoCascio, Riccardo G. et al., "Glycoprofiling of Bifidobacterial Consumption of Human Milk Oligosaccharides Demonstrates Strain Specific, Preferential Consumption of Small Chain Glycans Secreted in Early Human Lactation," Journal of Agricultural and Food Chemistry (2007) vol. 55, pp. 8914-8919.

International Preliminary Report on Patentability and Written Opinion of International Searching Authority for PCT/US2015/057226 dated May 4, 2017.

De Leoz et al., "Human Milk Glycomics and Gut Microbial Genomics in Infant Feces Show a Correlation between Human Milk Oligosaccharides and Gut Microbiota: A Proof-of-Concept Study," J. Proteome Research, American Chemical Society (2015) vol. 14, pp. 491-502.

Egan et al,. "Metabolism of Sialic Acid by Bifidobacterium breve UCC2003," Applied and Environmental Microbiology, (2014) vol. 80, No. 14, pp. 4414-4426.

Ng et al., "Microbiota-Liberated Host Sugars Facilitate Post-Antibiotic Expansion of Enteric Pathogens," Nature, (2013) vol. 502 (7469), pp. 96-99.

Underwood el al., "*Bifidobacterium longum* subspecies *infantis*: Champion Colonizer of the Infant Gut," Department of Pediatrics, Pediatric Research, University of California, Davis (2015) vol. 77, No. 1, pp. 229-235.

* cited by examiner

ACTIVATED BIFIDOBACTERIA AND METHODS OF USE THEREOF

CROSS-REFERENCE TO RELATED APPLICATIONS

This application is a U.S. National Phase Filing of International Patent Application PCT/US2015/057226 filed Oct. 23, 2015, which claims the benefit of priority to U.S. Provisional Patent Application 62/068,553, filed Oct. 24, 2014, and U.S. Provisional Patent Application No. 62/133,243, filed Mar. 13, 2015, the contents of each are hereby incorporated by reference in their entireties.

FIELD OF THE INVENTION

This invention relates generally to promoting health, and more particularly, to improving the human microbiome. Further, embodiments of this invention relate to activated bifidobacterial compositions, methods of making activated bifidobacteria, and the use of the compositions in order to initiate and maintain a human gut microbiome that is highly enriched in *Bifidobacterium* species in order to facilitate the development of a human infant's gastrointestinal (GI) tract and immune function.

BACKGROUND

When a vaginally-delivered human infant is breast-fed he/she will have a gastrointestinal microbiome that is unique in composition and diversity compared to any other time in their life. The GI microbiome is dominated by a single organism which can be present at high concentrations (up to and over 70% of the total microbiome). However, the obstetric standard of care in a typical hospital today involves births from both Cesarean Section (C-section) and vaginal delivery, followed by human milk or infant formula feeding for the baby. The surgical suite and levels of cleanliness for the mother pre- and post-op in many modern hospital settings are such that in many cases the infant will not get seeded with bacteria normally found in the microbiome of the vagina or gastrointestinal tract of the mother, resulting in a dysbiosis in the baby whether delivered by C-Section or vaginal births or fed by mother's milk or infant formula. Furthermore, dysbiosis can also be caused by infants losing the beneficial *Bifidobacterium* as a result of illness or medical intervention (e.g., antibiotic treatment). The dysbiosis of the infant microbiome leads to increased gastrointestinal problems and delayed or altered immunological programming and tolerization. The consequences of early dysbiosis are considered to have an impact throughout the entire life of that individual.

Human milk contains a significant quantity of complex oligosaccharides (up to 15% of total dry mass) in a form that is not usable as an energy source for the baby nor for most of the microorganisms in the gut of that baby. Certain microorganisms such as *Bifidobacterium longum* subsp. *infantis* [*B. infantis* or BI] have the unique capability to consume the specific complex oligosaccharides such as those found in human or bovine milk (U.S. Pat. No. 8,198,872 and U.S. Pub. No. 2013/0195803, the contents of which are incorporated herein by reference). When *B. infantis* comes in contact with certain complex oligosaccharides a number of genes are specifically induced within the bacterium whose protein products as enzymes and binding proteins are responsible for the uptake and internal deconstruction of those complex oligosaccharides, and the individual sugar components are then catabolized to provide energy for the growth and reproduction of that organism (Sela et al, 2008, *PNAS*, 105(48): p. 18964-69).

SUMMARY

The instant invention provides compositions comprising isolated complex oligosaccharide fractions from mammalian milk sources, optionally supplemented with purified fucosylated/sialylated oligosaccharides. The mammalian milk may be from human or bovine sources, and including but not limited to, the bovine source is from bovine colostrum. The fucosylated oligosaccharide(s) may comprise synthetically produced and purified 2'-fucosyllactose, 3-fucosyllactose, difucosyllactose, or lacto-N-fucosylpentose.

In some embodiments, the composition further comprises bifidobacteria that internalize the complex oligosaccharides or dietary glycans prior to their hydrolysis and metabolism. The combination of the bifidobacteria with the complex oligosaccharide may result in the conversion of the bifidobacteria to an activated bifidobacteria (ABI). The bifidobacteria is preferably selected from *B. longum, B. breve, B. bifidum* or *B. pseudocatenulatum*, and more preferably, the *B. longum* is *B. longum* subsp. *infantis*.

In other embodiments, any of the compositions described herein provide a method of improving the health of a mammal comprising administering to a mammal a composition comprising a complex oligosaccharide from a mammalian milk source, optionally supplemented with a fucosylated and/or sialylated oligosaccharide, and a bifidobacteria that internalizes the complex oligosaccharide prior to its hydrolysis, and wherein the fucosylated oligosaccharide can be a synthetically produced and purified form of 2'-fucosyllactose, 3-fucosyllactose, difucosyllactose, or lacto-N-fucosylpentose, wherein the bifidobacteria is preferably selected from *B. longum, B. breve, B. bifidum* or *B. pseudocatenulatum*, and more preferably, the *B. longum* is *B. longum* subsp. *infantis*. The bifidobacteria is typically provided in a daily dose of from 10 thousand to 100 billion cfu, preferably 1 billion to 50 billion, and most preferably 5 billion to 25 billion, and the oligosaccharides are provided in a daily dose of from 1 to 20 g, preferably in a daily dose of from 1 to 10 g.

DETAILED DESCRIPTION OF PREFERRED EMBODIMENTS

I. Introduction

Figure 1:
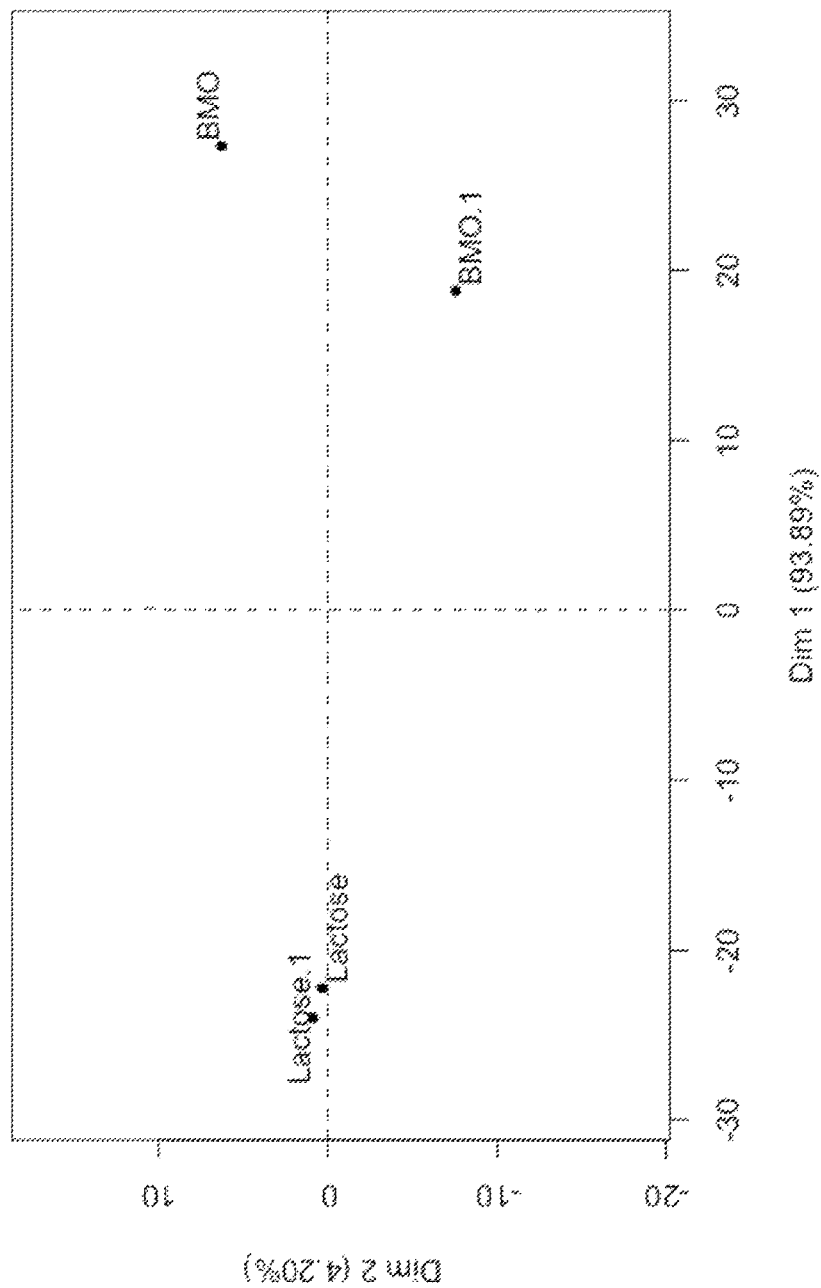
FIG. 1 is a diagram depicting whole genome expression analysis which shows differential gene expression of *B. infantis* cells grown in the presence of bovine milk oligosaccharides (BMO) or lactose.

Human milk glycans contain a significant quantity of human milk oligosaccharides (designated herein as "HMOs") (about 15% of total mass) in a form that is not usable as an energy source for the baby or for most of the microorganisms in the gut of that baby. HMOs can be found as free oligosaccharides (dietary glycans) or conjugated to protein or lipids. The major HMOs in milk include lacto- N-tetraose (LNT), lacto-N-neotetraose (LNnT) and lacto-N-hexaose, which are neutral HMOs, in addition to fucosylated oligosaccharides such as 2-fucosyllactose (2FL), 3-fucosyllactose (3FL), and lacto-N-fucopentaoses I, II and III. Acidic HMOs include sialyl-lacto-N-tetraose, 3' and 6' sialyllactose (6SL). HMOs are particularly highly enriched in fucosylated oligosaccharides (Mills et al., U.S. Pat. No. 8,197,872). Among the enzymes that produce HMOs in the mammary gland is the enzyme encoded by the fucosyltransferase 2 (FUT2) gene, which catalyzes the linking of fucose residues by an α1,2-linkage to oligosaccharides found in human milk. Fucosylated oligosaccharides are known to inhibit the binding of pathogenic bacteria in the gut. HMOs, and in particular the fucosylated HMOs, share common structural motifs with glycans on the infant's intestinal epithelia known to be receptors for pathogens. (German et al., WO 2012/009315)

HMOs are substrates for the selective growth of certain bifidobacteria in the mammalian gut. Certain bifidobacteria such as, but not limited to, *Bifidobacterium longum* subsp. *infantis* possess a gene cluster dedicated to the internalization and deconstruction of HMOs. When such bacteria interact with HMOs, this gene cluster, including genes for transporting and catabolizing fucosylated oligosaccharides, is upregulated. The interaction of certain HMOs with *B. longum* subsp. *infantis* has been shown to activate the bacterium by inducing expression of a number of genes including, but not limited to, those in the HMO gene cluster that encode proteins to capture and internalize the HMOs and encode enzymes to completely catabolize the HMOs, thereby providing that microbe with energy and substrate to grow and multiply (Underwood, 2015, *Pediatric Research*, 77(1-2):229-35). The products of the upregulated genes also allow *B. longum* subsp. *infantis* to colonize the mucosal lining of the gut and thereby impede the binding of pathogenic microbes. (Underwood, et al., 2015, *Pediatr. Res.*, 77:229-235). The activated bacterium has been shown to possess increased binding to intestinal epithethial cells. (Chichlowski et al., 2012, *J. Pediatric Gastroenteral Nur*, 55:321-327). The activated *B. longum* subsp. *infantis* is also able to produce short chain fatty acids which facilitate the development of the infant's mucosal lining and the immune system (Underwood et. al., 2015, *Pediatr Res*, 77: 229-235). Consequently, the proliferation of ABI in the gut of a newborn infant, triggered and uniquely enabled by the HMOs provided in mother's milk, is of significant benefit to the acute health and long term survival of that infant. Consequently, ABI provides significant benefits to a newborn infant which include, but are not limited to, a higher binding affinity to the gut mucosa, higher colonization of the GI tract thereby preventing growth of other bacterial clades, a higher production of short chain fatty acids, higher consumption of complex oligosaccharides, and a greater stimulation of the immune response as measured by positive alterations of immune response markers, relative to the organism in a pre-activated state (Lewis, et al., 2015, *Microbiome*, 3:13; Huda, et al., 2014, *Pediatrics*, 134:2 e362-e372).

In the activated form, the *B. infantis* becomes the sole consumer of the human milk oligosaccharides (HMO) and has been shown to increase its relative proportion in the gut microbiota of infant humans to levels at least 10-fold higher than its levels at birth (prior to consumption of HMO), or in those infants exclusively fed commercial infant formula not containing milk oligosaccharides, and reaching levels as high as 70% of the total microbial population of the distal colon of breast-fed babies. When *B. infantis* is present in the gut of a baby, and that baby is also provided with its mother's milk as a sole source of nutrition, the population of *B. infantis* can increase to levels as high as 90% of the total bacterial population of the gut as measured by the microbial quantification of the stool. The ABI will remain in the gut at high concentrations and remain activated as long as a dietary source of the selective complex oligosaccharides (e.g., HMO to human babies) is provided to the infant. Once the source of the complex oligosaccharides is withdrawn from the diet (e.g., at weaning and the introduction of solid foods), the *B. infantis* is no longer activated, it can no longer successfully compete other gut microbiota for nutrients in the gut, and its population decreases to less than 1% of the total microbiome. *B. infantis* is not normally found in the gut of a weaned infant, child, or adult in levels of more than 1% of the total microbiome Surprisingly, *B. infantis* has also been shown to grow on oligosaccharides isolated from bovine milk (German, et al., WO 2012/009315; Ward, 2009, *Open Glyceroscience*, 2:9-15). The concentration of oligosaccharides in bovine milk oligosaccharides that are selective in supporting the growth of *B. infantis* (designated as "BMO") is low in mature bovine milk compared to that of human milk. This difference in absolute concentration of oligosaccharides in milk may be due to an initially low level of BMO in mature bovine milk or due to the presence of enzymes in the milk that break down BMO into more simple sugars. Furthermore, the structural composition of the BMO is different from that of HMO (Aldredge et al., 2013, *Glycobiology*, (6):664-76; Mehra et al., 2014, *PLoS One*, 9(5):e96040). For example, BMOs are higher in sialic acid-rich components than HMOs and lower in fucose-rich components than HMOs (Zivkovic and Barile, 2011, *Advance Nutrition*, (3): 284-289).

Recently, the inventors have found that *B. infantis* and *B. breve*, which are human-associated bacteria, are activated by bovine colostrum oligosaccharides (BCO), such as those found in a bovine colostrum oligosaccharide concentrate (BCOC). Colostrum is a special fluid that comes from the breast of mammals (e.g., humans and bovines) during the first few days after giving birth. The composition of colostrum is significantly different from that of the mature milk which replaces the colostrum after the first few days of lactation. Bovine colostrum oligosaccharides (BCOs) or bovine colostrum oligosaccharide concentrates (BCOs) have a composition that is different from HMO and BMO (U.S. Provisional Application No. 62/155,553, incorporated by reference herein; Tao et al., 2009, *Journal of Dairy Science*, 92:2991-3001). For example, BCO is highly enriched in sialic acid residues but is deficient in many fucosylated oligosaccharides compared to mature milk BMO. The inventors also discovered that there are a large number of genes in addition to the HMO gene cluster that are either up-regulated or down-regulated upon the interaction of *B. longum* subsp. *infantis* with the different oligosaccharides. Some of these genes are regulated by HMO and some by BMO, BCO, or BCOC, and some, like the HMO cluster, are regulated by both.

II. Definitions

The term "oligosaccharide" refers to polymeric carbohydrates that contain 3 to 20 monosaccharides covalently linked through glycosidic bonds. In some embodiments, the oligosaccharides are purified from human or bovine milk/whey/cheese/dairy products, (e.g., purified away from oligosaccharide-degrading enzymes in bovine milk/whey/cheese/dairy products).

The term "isolated," when applied to an oligosaccharide, refers to an oligosaccharide composition that has been at least enriched for the oligosaccharide compared to one or more other components in the mammalian milk. In some embodiments, the oligosaccharide(s) is purified, e.g., such that the oligosaccharide has been separated at least in part from one or more of the other components of milk.

The term "bifidobacteria" and its synonyms refer to a genus of anaerobic bacteria having beneficial properties for humans. Bifidobacteria is one of the major taxonomic groups of bacteria that make up the gut flora, the bifidobacteria are among the beneficial commensal bacteria that reside in the gastrointestinal tract and have health benefits for their hosts.

The term "synthetic" composition refers to a composition produce by a chemi-synthetic process and can be nature-identical. For example, the composition can include ingredients that are chemically synthesized and purified or isolated. This does not include compositions that are naturally synthesized by mammals.

The term "residues," when applied to an oligosaccharide, refers to monosaccharide residues of oligosaccharides joined through glycosidic linkages, which can be hydrolyzed by enzymes or acid to give the constituent monosaccharide units.

III. Compositions

The compositions described herein comprise a non-pathogenic microbe and/or at least one complex oligosaccharide that induces a change in the non-pathogenic microbe such that the complex oligosaccharide then becomes an energy source for the microbe, and when ingested by a mammal, the induced or activated microbe provides a benefit to the gut of that mammal.

A. Complex Oligosaccharide

In various embodiments, the composition comprises a plurality of oligosaccharides. The oligosaccharide composition may be derived from human and non-human glycan sources and may exist as free glycans or protein-bound glycans. In some embodiments, the oligosaccharide can be a bovine or human milk oligosaccharide. In some embodiments, the oligosaccharide composition comprises bovine milk oligosaccharides (BMOs). Bovine oligosaccharides may comprise oligosaccharides from mature milk, early milk, colostrum, or concentrates thereof. In some embodiments, the oligosaccharides can include, but are not limited to, fucose, sialic acid, N-acetylglucosamine, and/or gluconate residues.

In various embodiments, complex milk oligosaccharides include an oligosaccharide consisting of 3 Hex moieties, 4 HexNAc moieties and 1 fucose (Fuc) moiety; an oligosaccharide consisting of 4 Hex moieties, 4 HexNAc moieties, and 1 Fuc moiety; an oligosaccharide consisting of 3 Hex moieties, 5 HexNAc moieties, and 1 Fuc moiety; an oligosaccharide consisting of 5 Hex moieties, 4 HexNAc moieties, and 1 Fuc moiety; an oligosaccharide consisting of 4 Hex moieties, 5 HexNAc moieties, and 1 Fuc moiety; an oligosaccharide consisting of 3 Hex moieties, 6 HexNAc moieties, and 1 Fuc moiety; an oligosaccharide consisting of 3 Hexose (Hex) moieties and 6 N-acetyl hexosamine (HexNAc) moieties; an oligosaccharide consisting of 4 Hex moieties and 3 HexNAc moieties; an oligosaccharide consisting of 3 Hex moieties and 4 HexNAc moieties; an oligosaccharide consisting of 6 Hex moieties and 2 HexNAc moieties; an oligosaccharide consisting of 4 Hex moieties and 4 HexNAc moieties; an oligosaccharide consisting of 3 Hex moieties and 5 HexNAc moieties; an oligosaccharide consisting of 5 Hex moieties and 4 HexNAc moieties; an oligosaccharide consisting of 4 Hex moieties and 5 HexNAc moieties; and an oligosaccharide consisting of 3 Hex moieties and 6 HexNAc moieties. Exemplary oligosaccharides include Lacto-N-Tetraose, Lacto-N-Neotetraose, Lacto-N-Fucopentaose I, Lacto-N-Fucopentaose II, Lacto-N-Fucopentaose III, Lacto-N-Fucopentaose V, Lacto-N-Hexaose, Para-Lacto-N-Hexaose, Lacto-N-Neohexaose, Para-Lacto-N-Neohexaose, Monofucosyllacto-N-Hexaose II, Isomeric Fucosylated Lacto-N-Hexaose (1), Monofucosyllacto-N-Hexaose, Isomeric Fucosylated Lacto-N-Hexaose (3), Isomeric Fucosylated Lacto-N-Hexaose (2), Difucosyl-Para-Lacto-N-Neohexaose, Difucosyl-Para-Lacto-N-Hexaose, Difucosyllacto-N-Hexaose, Lacto-N-Neoocataose, Para-Lacto-N-Octanose, Iso-Lacto-N-Octaose, Lacto-N-Octaose, Monofucosyllacto-Nneoocataose, Monofucosyllacto-N-Ocataose, Difucosyllacto-N-Octaose I, Difucosyllacto-N-Octaose II, Difucosyllacto-N-Neoocataose II, Difucosyllacto-N-Neoocataose I, Lacto-N-Decaose, Trifucosyllacto-N-Neooctaose, Trifucosyllacto-N-Octaose and Trifucosyl-Iso-Lacto-N-Octaose.

In some embodiments, the oligosaccharide described herein comprises three or more monosaccharides (i.e., at least a trisaccharide), and can be a bovine or human milk glycan, or the equivalent thereof that is chemically synthesized. The complex oligosaccharide may be, but is not limited to, (3Hex,4HexNAc,1Fuc), (1Gal,1GlcNAc, 1NeuAc), and/or (1Glu,1Gal,1NeuAc (3' or 6')).

In some embodiments, the oligosaccharide described herein comprises any of Hex(4); Hex(4) HexNAc(2); and Hex(3) HexNAc(1) NeuAc(1) at levels greater than 1%. In another embodiment, the at least one oligosaccharide comprise one of the following ratios of constituents: 1) a ratio of Hex(2) NeuAc(1):Hex(2) HexNAc(1) less than 5.0; 2) a ratio of Hex(2) HexNAc(1):Hex (3) HexNAc(1) of greater than 1.0; 3) a ratio of Hex(2) HexNAc(1):Hex (3) HexNAc (2) of greater than 2.0; 4) a ratio of Hex(3):Hex (3) HexNAc (1) NeuAc(1) of less than 100; and 5) a ratio of Hex(2) HexNAc(1):Hex (4) NeuAc(2) NeuGc(1) of greater than 10.

Complex mammalian milk oligosaccharides (MMO) can be isolated from any number of sources and using methods known to those of skill in the art. For example, HMOs can be obtained from human milk using methods known in the art. Human milk may be provided by the International Milk Bank (Sparks, Nev., USA) or any such equivalent milk bank. Human milk may be pasteurized and then centrifugally defatted, separating it into cream (predominantly fat) and skim (defatted product). The defatted skim milk may then be filtered using membranes with a 5-10 kDa cut off to concentrate a protein fraction (predominantly whey) and the permeate, comprising the complex HMOs. The composition of this dried HMO fraction is about 50% lactose and about 30% HMO with the remainder of the mass primarily peptides and ash. The HMO fraction is predominantly fucosylated. The permeate may be further passed through a 1 kDa cut off filter to remove lactose and provide a more enriched HMO fraction in the retentate prior to spray drying. BMOs can be isolated similarly, using any number of sources and methods known to those of skill in the art. For example, BMO can be isolated using the purification protocols as disclosed in the US Pub. No. 20130035481, the contents of which are incorporated herein by reference.

Colostrum oligosaccharides (COs) can be isolated from mammalian sources such as, but not limited to cows (BCO), humans (HCO), goats (CCO), or sheep (OCO) and used in the instant invention. Colostrum can be used as whole colostrum or processed to selectively enrich the CO fraction. Processing steps could include, but are not limited to, pasteurization, centrifugation, precipitation, ultrafiltration and spray drying. In general, the processes are selected to remove, inhibit or destroy enzymes that degrade the COs. In some embodiments, additional processing steps can be used to sterilize the product to eliminate any potential bacterial or viral contamination. Such steps include, but are not limited to, conventional pasteurization, ultrahigh temperature (UHT) processes, gamma irradiation, freezing and thawing, sonication, and microfluidic disruption. In other embodiments, the lactose content of the BCO may be reduced using processes know in the art such as, but not limited to, the treatment of the extract with enzymes to degrade lactose or through mechanical or biological means of selective removal of lactose. In yet other embodiments of the invention, the liquid CO mixtures are concentrated and/or dried by processes such as, but not limited to, spray drying, freeze drying, fluid bed drying, tunnel drying, and drum drying.

In various embodiments, the complex oligosaccharide comprises at least 5%, 10%, 15%, 20%, 25%, 30%, 35%, 40%, 45%, 50%, 55%, 60%, 65%, 70%, 75%, 80%, 85%, 90%, or at least 95% of the dry weight of the composition.

In alternate embodiments, the complex oligosaccharide further comprises synthetically produced oligosaccharides comprising fucosyllactose (SPF) and/or synthetically-produced sialyllactose (SPS) or derivatives thereof including, but not limited to, 2'-fucosyllactose, 3-fucosyllactose, difucosyllactose, lacto-N-fucosylpentaose I, lacto-N-fucosylpentaose II, lacto-N-fucosylpentaose III, lacto-N-fucosylpentaose V, 3'-sialyllactose, 6'-sialyllactose, 3'-sialyl-3-fucosyllactose, sialyllacto-N-tetraose, and 6'-sialyllactosamine. The synthetically produced oligosaccharides (SPO) may be derived using any of the number of sources and methods known to those of skill in the art. For example, SPF is produced using protocols as disclosed in the US Pub. No. 20130035481, the contents of which are incorporated herein by reference.

The synthetically-produced oligosaccharides (SPOs) can be added to the biologically produced mammalian milk oligosaccharide (MMO) and make up from at least 5% to at least 80% of the dry weight of the composition. In some embodiments, the composition comprises a mixture of MMO and SPF and/or SPS. In various embodiments, the SPO is 1%, 5%, 10%, 15%, 20%, 25%, 30%, 35%, 40%, 45%, 50%, 55%, 60%, 65%, 70%, 75%, 80%, 85%, or 90% of the dry weight of the composition. In some embodiments, the SPF is 1-50% of the dry weight of the composition. In other embodiments, the SPO is 5-30% of the dry weight of the composition. In other embodiments, the SPO is 10-20% of the dry weight of the composition. The MMO comprises at least 1%, 5%, 10%, 15%, 20%, 25%, 30%, 35%, 40%, 45%, 50%, 55%, 60%, 65%, 70%, 75%, 80%, 85%, 90%, or at least 95% of the dry weight of the composition. In some embodiments, the MMO comprises BCOs wherein the BCOs comprise at least 20% of the dry weight of the composition. In another preferred embodiment, the BCOs comprise at least 50% of the dry weight of the composition. In another preferred embodiment, the BCOs comprise at least 70% of the dry weight of the composition. In some embodiments, the mass ratio of MMO:SPO is from 20:1 to 1:10. In some embodiment, the ratio is from 10:1 to 1:2, and in another embodiment, the ratio is from 5:1 to 1:1. In some examples, the ratio is about 10:1, about 9:1, about 8:1, about 7:1, about 6:1, about 5:1, about 4:1, about 3:1, about 2:1, about 1:1, about 1:2 about 1:4, about 1:5, about 1:6 about 1:3, about 1:3, 10:2, about 9:2, about 8:2, about 7:2, about 6:2, about 5:2, about 4:2 or about 3:2.

B. Non-Pathogenic Microbes

In various embodiments, the composition comprises one or more species of non-pathogenic microbes, where one of the non-pathogenic microbes is from a species whose genome encodes a transport system capable of internalizing one or more complex oligosaccharides before the oligosaccharide is internally hydrolyzed. In various embodiments, the microbe is from the genus *Bifidobacterium*. The species may be, but is not limited to, *B. longum, B. bifidum, B. breve, B. pseudocatenulatum, B. catenulatum*, or any *Bifidobacterium* strain that expresses a fucosidase, or any combination of these *Bifidobacterium* species. In some embodiments, one of the species is *Bifidobacterium longum* and in preferred embodiments, one or both of the species is *Bifidobacterium longum* subspecies *infantis*.

In various embodiments, the *Bifidobacterium* may comprise activated *Bifidobacterium* (ABI). The activated *Bifidobacterium* is defined herein as the state of the cells, as measured by the up-regulation or down-regulation of genes including but not limited to those coding for oligosaccharide binding proteins, transport proteins, and enzymes responsible for the degradation of the complex oligosaccharides, which provides significant benefits to a newborn infant. Such beneficial characteristics of the ABI include, but are not limited to, a higher binding affinity to the gut mucosa, higher colonization of the GI tract thereby preventing growth of other bacterial clades, a higher production of short chain fatty acids, the ability to consume complex oligosaccharides, and a greater stimulation of the immune response as measured by positive alterations of immune response markers, relative to the organism in a pre-activated state (Lewis, et al., 2015, *Microbiome*, 3:13; Huda, et al., 2014, *Pediatrics*, 134:2 e362-e372).

In various embodiments, the bifidobacteria encodes gene clusters containing ATP-binding cassette (ABC) transporters and glycosyl hydrolases involved in HMO utilization, typically including one or more genes coding for a fucosidase. In some embodiments, the bifidobacteria contains a gene coding for a complex oligosaccharide transporter. In some embodiments, the bifidobacteria contains a gene coding for a fucose transporter. In some embodiments, the bifidobacteria contains a gene coding for a fucose or sialic acid transporter. In many embodiments, the genes encoding these components are upregulated or expressed. The genes may be constitutively upregulated or induced.

Certain biomarkers may be induced and/or repressed as markers to predict an activated state for *bifidobacterium* species, whereby the bacteria are optimally primed for complex oligosaccharide consumption. Suitable biomarkers identified with *B. longum* subsp. *infantis* activation include upregulated genes and downregulated genes. Exemplary upregulated genes include Blon_0042 (regulatory protein); Blon_R0015 (tRNA); Blon_R0017 (tRNA); Blon_R0021 (tRNA); and Blon_R0022 (tRNA). Exemplary downregulated genes include Blon_0518 (hypothetical protein); Blon_0785 (membrane lipoprotein (possible transporter component)); Blon_2167 (hypothetical protein); and Blon_2168 (phage shock protein C). Previously, these genes were not known to be associated with an activated cell.

In some embodiments, the activated bifidobacteria comprises gene Blon_0042, wherein gene Blon_0042 has been upregulated. The activated bifidobacteria may comprise gene Blon_2168, wherein gene Blon_2168 has been downregulated. In one embodiment, the activated bifidobacteria comprises gene Blon_0042 and gene Blon_2168, wherein gene Blon_0042 has been upregulated and gene Blon_2168 has been downregulated. The skilled person can readily adapt quantitative proteomic methods to determine the expressed levels of the gene products (e.g., mRNA and protein) for these genes, to confirm activation.

ABI is activated by being cultivated in a medium comprising at least one oligosaccharide among the complex oligosaccharides described above for a sufficient period of time to undergo induction and biosynthesis of at least one metabolic enzyme. The oligosaccharides are typically sourced from, or are identical to, those mammalian milk oligosaccharides (MMOs) including, but not limited to, those from human milk and bovine milk. In some embodiments, the oligosaccharide can be a bovine or human milk oligosaccharide. In another embodiment, the oligosaccharide is obtained from mammalian colostrum. In some embodiments, the oligosaccharide composition comprises bovine milk oligosaccharides (BMOs). Bovine oligosaccharides may comprise oligosaccharides from mature milk, early milk, colostrum, or concentrates thereof. In some embodiments, the oligosaccharides include fucose as component saccharide residues. In an alternative embodiment, the MMO is supplemented with synthetically produced and purified oligosaccharides comprising fucosylated and/or sialylated oligosaccharides. In some embodiments of the invention, the synthetically-produced fucosyllactose (SPF), sialyllactose (SPS) or derivatives thereof are used to activate bifidobacteria in a way that is more human-like than when activated by BMOs alone. In another embodiment, the composition is used to upregulate operons other than the HMO cluster.

Any of the compositions described herein may be prepared by cultivating a bifidobacteria in an axenic culture (e.g., a culture with genetic homogeneity), the culture comprising bovine milk glycans, (e.g., concentrated from bovine colostrum) to become "activated." In various embodiments, any of the compositions described herein can be made by isolating bifidobacteria; purifying the bacteria; inoculating a fermenter with the purified strains of the bifidobacteria; and culturing the bifidobacteria in the presence of complex bovine or human oligosaccharides; and harvesting the cells. Fermentations for bifidobacteria may be carried out in stirred tank fermenters of commercial volume (e.g., 1-500 $m^3$) which are maintained under anaerobic conditions throughout the fermentation process. The fermentation can include the steps of providing at least one complex oligosaccharide at any time during the course of the fermentation in a liquid culture at a level of at least 1 g/L, typically from about 1-50 g/L, or 2-20 g/L, or 5-10 g/L as a sole, or supplementary, carbon source to activate the cells.

The bifidobacteria described herein may be tested for its ability to use bovine or human milk oligosaccharides for growth. In some embodiments, the bifidobacteria are capable of growing on mammalian milk glycans where less than 20% of the sialic acid content and 20% of the fucose content of the milk glycans remains after a culture of the composition has ceased to grow. In some embodiments, the composition is capable of growing on mammalian milk oligosaccharide wherein less than 10% of the sialic acid content and 10% of the fucose content of the milk glycans remains after a culture of the composition has ceased to grow. In a preferable embodiment the composition is capable of growing on milk glycans wherein less than 5% of the sialic acid and 5% of the fucose of the milk oligosaccharides remains after a culture of the composition has ceased to grow. In a particularly preferable embodiment, the composition is capable of growing on milk glycans wherein less than 1% of the sialic acid and 1% of the fucose of the milk oligosaccharides remains after a culture of the composition has ceased to grow.

In a further embodiment, the composition can comprise a total count of viable bacteria from about 100 thousand to 500 billion colony forming units (cfu) per gram dry weight. In another embodiment, the total count of viable bacteria comprises 5 billion to 100 billion cfu per gram dry weight. In another embodiment, the total count of viable bacteria comprises 10 billion to 50 billion cfu per gram dry. In some embodiments, the ABI concentration is from 10 to 100 g dry weight per liter. The fermentation products can also be concentrated by filtration or centrifugation. The ABI can be can be dried by controlled desiccation processes such as, but not limited to, freeze drying.

IV. Formulating Compositions

The composition comprising MMO and ABI can be prepared by mixing the two components together. Optionally, one can combine the harvested and/or dried activated bifidobacteria cells with a powdered form of a complex bovine or human milk oligosaccharide. The harvested and/or dried activated bifidobacteria cells and the powdered form of the complex bovine or human milk oligosaccharide can be in a single dose packet, which can contain from about 10 million to about 100 billion cfu of bacteria and, optionally, from about 0.5 g to about 5 g of complex oligosaccharide. The complex bovine oligosaccharide can be present in a powder composition wherein the blend ratio of activated bifidobacteria cells to complex oligosaccharide is 30 billion cfu per 1.5 g complex oligosaccharide in a powder form.

Any of the compositions described herein can further comprise a secondary metabolite. The secondary metabolite can be a short chain fatty acid, such as acetate, lactate, or combinations thereof. The compositions described herein can further comprise a stabilizer, such as a flow agent. Flow agents may include starch, silicon dioxide, tricalcium phosphate, powdered cellulose, magnesium stearate, sodium bicarbonate, sodium ferrocyanide, potassium ferrocyanide, calcium ferrocyanide, bone phosphate, sodium silicate, calcium silicate, magnesium trisilicate, talcum powder, sodium aluminosilicate, potassium aluminum silicate, calcium aluminosilicate, bentonite, aluminum silicate, stearic acid, and polydimethylsiloxane. The stabilizer can be a milk protein or another suitable pharmaceutical grade or infant formula grade diluent (e.g., lactose). The milk protein can comprise a protein fraction of non-fat dry milk.

Any of the compositions described herein can further comprise surface carbohydrate binding protein (e.g., solute binding proteins). The surface carbohydrate binding proteins can allow a more effective binding and interaction with the gut mucosa by binding to cell surface glycosylation of the gut mucosa and or mucous layers. This binding of surface carbohydrate can then exclude the binding of pathogenic bacteria.

In various embodiments, any of the compositions described herein may be dried (e.g., by spray-drying or freeze-drying), and formulated into a unit dose medicament, such as a packet, sachet, orally disintegrating tablet, foodstuff, capsule, lozenge, effervescent tablet, etc. The unit dose medicament can be formed from a variety of materials including without limitation plastic, or paper. In some embodiments, the unit dose medicament comprises a moisture barrier and/or oxygen barrier layer. Alternatively, the composition may be provided in a form for anal delivery, such as a suppository or in an enema. Preferably, the composition is packaged in sachets made using a moisture and/or oxygen impermeable polymer.

In various embodiments, any of the compositions described herein may be provided in a dry powder formulation, a solution, a suspension, or in a tablet or capsule format with or without an enteric coating. The dry powder can be freeze-dried or spray dried. The freeze-dried compositions are preferably frozen in the presence of a suitable cryoprotectant. The cryoprotectant can be, for example, glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidone, or taurine. The enteric coatings include, but are not limited to, fatty acids, waxes, shellac, plastics, plant fibers, methyl acrylate-methacrylic acid copolymers, cellulose acetate succinate, hydroxy propyl methyl cellulose phthalate, hydroxy propyl methyl cellulose acetate succinate, polyvinyl acetate phthalate (PVAP), methyl methacrylate-methacrylic acid copolymers, cellulose acetate trimellitate, sodium alginate, and Zein.

In some embodiments, the microbe is mixed with a cryopreservative such as but not limited to trehalose or glycerol under anaerobic conditions and frozen by processes such as, but not limited to, rapid freezing (chilling with liquid nitrogen), or by a controlled temperature reduction in a cryopreservation freezing system. Once frozen, the microbes can be dehydrated under vacuum using a process that best maintains the integrity of the microbe cells. The microbe concentration in the dry powder can be from 1 million to 500 billion cfu/g. In some embodiments, the dry powder can be from 5 billion to 100 billion cfu/g, and in a most preferred embodiment the dry powder can be from 10 billion to 50 billion cfu/g.

In some embodiments of the invention, the powdered microbe is resuspended in an edible oil such as, but not limited to triglyceride oils (e.g., vegetable oil, olive oil, and medium chain triglycerides), diglyceride oils, monoglyceride oil, and silicone oils.

In various embodiments, the oligosaccharide composition can be dissolved in a polar liquid such as, but not limited to, water, physiological saline, mammalian milk, or an infant formula, and provided in a liquid form to the infant while the bifidobacteria are provided separately as a powder or suspension in a carrier liquid which may include a solution comprising the oligosaccharide.

In various embodiments, the microbes and the oligosaccharide composition may be provided combined or provided separately. In some embodiments, the microbe is combined with an oligosaccharide in a single dose packet containing from about 1 to about 100 billion cfu of microbe and from about 0.5 to about 5 g of an oligosaccharide.

V. Use of Compositions for Improvement of Mammalian Health

In various embodiments, the compositions described herein are delivered as a pre-activated and purified composition of *bifidobacterium* to a subject in need thereof substantially contemporaneously with delivery of compounds to the mammalian intestine to make the intestinal environment a more favored niche to the aforementioned purified composition of bifidobacteria, where the compounds may comprise complex oligosaccharides described above, synthetically produced and purified oligosaccharides, and/or secondary metabolites produced as a result of intestinal fermentation.

In various embodiments, the use described herein comprises monitoring the subject's intestinal microbiome before, during and/or after administration of the composition described herein. A variety of monitoring techniques are known to one of ordinary skill in the art. For example, a routine sample of the subject's feces may be analyzed for microbes qualitatively and/or quantitatively by standard processes well known in the art (see, e.g., Le Pare et al., 2014, *Food and Nutrition Sciences,* 5: p. 71-78).

In some embodiments, the compositions described herein are administered to a subject in need thereof in an amount and for a duration effective to establish the population of bifidobacteria at high levels in the gastrointestinal tract of the subject. In some embodiments, the compositions described herein can be administered to a subject in need thereof in an amount and for a duration effective to maintain the population of bifidobacteria at high levels in the gastrointestinal tract of the subject. In some embodiments, the composition is administered daily in an effective amount to maintain the bifidobacteria population in the gut of the subject at greater than at least 5%, 10%, 20%, 30%, 40%, 50%, 60%, 70%, 80%, or at least 90% of the total fecal microbiome of the mammal.

In some embodiments, the composition comprising activated bifidobacteria is administered to a subject in need thereof. In other embodiments, the composition comprising complex oligosaccharides supplemented with synthetically produced and purified oligosaccharide is administered to a subject in need thereof. In another embodiment, the composition comprising both activated bifidobacteria and complex oligosaccharide is administered to a subject in need thereof. In another embodiment, the composition comprising bifidobacteria, and complex oligosaccharides supplemented with synthetically produced and purified oligosaccharide is administered to a subject in need thereof.

In various embodiments, the bifidobacteria are administered at a dose of from 1 billion to 100 billion cfu of bifidobacteria and from 1 to 20 g of complex oligosaccharides per day. In some embodiments, a dose is administered from 5 to 50 billion cfu/day. In another embodiment, a dose is administered from 5 to 100 billion cfu/day. In another embodiment, the dose is administered from 10 to 25 billion cfu/day. In various embodiments, the complex oligosaccharide is administered in a dose of from 0.5 g to 5.0 g/day. In some embodiments, the dose is administered in a dose from 1.0 g to 3.0 g/day.

Typically, the composition of this invention is presented as a single, unit dose package that is administered once per day. However, the doses may be presented in multiple (e.g., two, three, four, five, six, or more) sub-doses administered at appropriate intervals throughout the day. Alternatively, they may be administered in the same composition, or constituent components may be administered sequentially. In some embodiments, the treatment is maintained for a period of at least 1-week, 2-weeks, 3-weeks, or at least 4-weeks. In other embodiments, the treatment is administered for a period of from at least 2-months, 4-months, 6-months, 8-months, 10-months, or at least 12-months.

The subject in need thereof can be, for example, an infant from birth to about 36 months post-conception. In additional embodiments, the compositions described herein may be administered to a pregnant woman in at least the third trimester of pregnancy. The composition administered during pregnancy may include either the bifidobacteria, the oligosaccharide, or both. In additional embodiments, the composition described herein is administered in a therapeutic amount to an infant born vaginally or by cesarean section. The compositions described herein are administered to the infant immediately after delivery and thereafter for at least the first month to six months of the life of the infant. The composition may be administered directly to the infant or mixed with a liquid including, but not limited to breast milk, infant formula, physiological saline, or water. For infants who are not breast fed, the compositions described herein may alternatively be administered in an infant formula and such compositions may preferably comprise both activated B. infantis and a milk-derived oligosaccharide. For infants born via cesarean section, compositions comprising of activated bifidobacteria and/or complex oligosaccharides may be administered. For infants born vaginally, compositions comprising activated bifidobacteria and/or complex oligosaccharides may be administered.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

EXAMPLES

The following examples are offered to illustrate, but not to limit the claimed invention.

Example 1. Preparation of Human Milk Oligosaccharide (HMO) Compositions that can be Used Exclusively by Certain Bifidobacteria A concentrated mixture of HMO is obtained by a process similar to that described by Fournell et al (US Patent Application 20150140175). Human milk is pasteurized and then centrifugally defatted, separating it into cream (predominantly fat) and skim milk (defatted product). The defatted skim milk is then ultrafiltered using membranes with a 5-10 kDa cut off to concentrate a protein fraction (predominantly whey). The permeate from the ultrafiltration, comprising the complex HMOs, is dried by spray drying. The composition of this dried fraction is about 50% lactose and about 30% complex oligosaccharides (HMO) with the remainder of the mass primarily peptides and ash. The HMO fraction is predominantly fucosylated.

This method or similar methods can be used to obtain compositions containing isolated complex oligosaccharides from any mammalian milk source. For example, complex oligosaccharides can be isolated using the purification protocols as disclosed in the US Pub. No. 20130035481, the contents of which are incorporated herein by reference. Such compositions are suitable for use in embodiments of this invention.

Example 2. Preparation of Bovine Colostrum Oligosaccharide (BCO) Compositions and Compositions Supplemented with Synthetically Produced and Purified Fucosylated Oligosaccharides (SPF) that can be Used Exclusively by Certain Bifidobacteria A concentrated mixture of bovine colostrum oligosaccharide is obtained by a process such as that described by Christiansen et al (2010) International Dairy Journal, 20:630-636. Bovine colostrum (preferably from the first milking) is pasteurized by heating to 145 degrees F. for 30 minutes, cooled and centrifugally defatted, separating it into cream (predominantly fat) and skim milk (defatted product). The defatted skim milk is then ultra-filtered using membranes with a 5-10 kDa cut off to concentrate a protein fraction (predominantly whey). The whey permeate is further microfiltered using a 1 kDa cut off to remove some lactose and concentrate the oligosaccharides in the retentate. The final composition is spray dried to produce a dried oligosaccharide fraction having about 40% lactose and about 40% complex oligosaccharides (BCO) with the remainder of the mass primarily peptides and ash. The BCO fraction is predominantly sialylated.

Synthetically produced and purified fucosylated oligosaccharides (SPF) can be can be obtained commercially from any of the number of sources or derived by methods known to those of skill in the art. 100 g of purified 3-Fucosyllactose (SPF; Elicityl SA, Crolles, FR) may be added to 1 kg of the BCO preparation and thoroughly mixed to produce a BCO/SPF composition with a ratio of BCO:SPF of about 4:1. The sample is analyzed and the complex oligosaccharide component is about 20% fucosylated oligosaccharides.

This method or similar methods can be used to obtain compositions containing complex oligosaccharides from any mammalian milk source supplemented with particular synthetic oligosaccharides. Such compositions are suitable for use in embodiments of this invention.

Example 3. Differentiation Between BCO, BCOC, BMO and HMO Fractions

A BCOC fraction was commercially obtained as Immunel, (Sterling Technology, USA) and analyzed using HPLC-MS methods of Tao et al (2008) J Dairy Science, 92: 2991-3001 and compared in Table 1 with oligosaccharide fractions from human milk (HMO), mature bovine milk (BMO) and bovine colostrum (BCO). The four compositions in Table 1 are significantly different from each other and several features are immediately apparent. BCOC contains several oligosaccharides that are not found in BMO, BCO or HMO such as Hex(4) and Hex(3) HexNAc(1) NeuAc(1), and several oligosaccharides that are found in BCO and BMO are not present in BCOC such as Hex(2) HexNAc(1) NeuAc(1), Hex (3) HexNAc(2), and Hex (4) NeuAc(2) NeuGc(1).

TABLE 1

Key oligosaccharides that differentiate colostrum and BMO compositions as disclosed in Tao (2009), HMO compositions as disclosed in Mills et al (2012) and bovine colostrum oligosaccharide concentrate (BCOC; Immunel) of the instant invention. Values listed are percentages of the total sample oligosaccharides.

| m/z reduced neutral | Hex | HexNac | NeuAc | NeuGc | Fuc | BCO Tao | BCOC | BMO Tao | HMO |
|---|---|---|---|---|---|---|---|---|---|
| 506.1833 | 3 | | | | | 2.27 | 22.70 | 18.70 | 1.48 |
| 547.2198 | 2 | 1 | | | | 2.62 | 17.10 | 1.59 | 0.01 |
| 635.2263 | 2 | | 1 | | | 20.33 | 26.00 | 22.61 | 1.82 |
| 667.2300 | 4 | | | | | 0.10 | 1.40 | 0.01 | 0.01 |
| 676.2533 | 1 | 1 | 1 | | | 4.47 | 3.90 | 1.01 | 0.01 |
| 709.2621 | 3 | 1 | | | | 4.15 | 6.90 | 10.00 | 20.90 |
| 750.2892 | 2 | 2 | | | | 5.62 | 3.30 | 0.01 | 0.01 |
| 797.2772 | 3 | | 1 | | | 4.98 | 3.20 | 23.11 | 0.01 |
| 838.3056 | 2 | 1 | 1 | | | 3.34 | 0.01 | 0.61 | 0.01 |
| 855.3221 | 3 | 1 | | | 1 | 0.01 | 0.01 | 0.01 | 0.70 |
| 871.3153 | 4 | 1 | | | | 7.35 | 7.50 | 12.46 | 0.01 |
| 912.3409 | 3 | 2 | | | | 4.73 | 0.01 | 2.85 | 0.01 |
| 942.3234 | 2 | | 1 | 1 | | 11.48 | 0.01 | 0.01 | 0.01 |
| 999.3517 | 3 | 1 | 1 | | | 0.01 | 1.30 | 0.01 | 0.01 |
| 1074.3960 | 4 | 2 | | | | 0.01 | 4.50 | 0.52 | 0.41 |
| 1177.4000 | 4 | | 1 | 1 | | 2.63 | 0.01 | 0.26 | 0.01 |
| 1220.4540 | 4 | 2 | | | 1 | 0.01 | 0.01 | 0.01 | 25.20 |
| 1366.5120 | 4 | 2 | | | 2 | 0.01 | 0.01 | 0.01 | 13.50 |
| 1439.5290 | 5 | 3 | | | | 0.01 | 0.01 | 0.01 | 2.00 |
| 1585.5870 | 5 | 3 | | | 1 | 0.01 | 0.01 | 0.01 | 5.90 |
| 1731.6450 | 5 | 3 | | | 2 | 0.01 | 0.01 | 0.01 | 7.20 |
| 1804.6610 | 6 | 4 | | | | 0.01 | 0.01 | 0.01 | 1.40 |
| 1877.7030 | 5 | 3 | | | 3 | 0.01 | 0.01 | 0.01 | 5.00 |
| 1950.7190 | 6 | 4 | | | 1 | 0.01 | 0.01 | 0.01 | 2.90 |
| 2096.7770 | 6 | 4 | | | 2 | 0.01 | 0.01 | 0.01 | 3.60 |
| 2242.8350 | 6 | 4 | | | 3 | 0.01 | 0.01 | 0.01 | 1.80 |

In addition, the ratios of the various bovine oligosaccharides to each other are also quite different among the bovine sources as demonstrated in Table 2. The ratio of Hex(3) to Hex(3) NeuAc(1) of BCOC is greater than 1.0, the ratio of Hex(3) to Hex(4) HexNAc(2) of BCOC is less than 20, and the ratio of Hex(2) HexNAc(1) to Hex(4) of BCOC is less than 20. Further, these bovine oligosaccharide compositions are all distinguished from HMO in that in addition to the ratio differences all bovine oligosaccharide samples are further characterized by being less than 50% fucosylated. In addition, about 70% of bovine early milk oligosaccharides are sialylated in contrast to 50% in BMO, HMO, and N-glycolylneuraminic acid, which made up 7% of the sialic acid in the bovine early milk is completely absent in mature BMO (Tao, 2009). Even without specifying fucosylation or sialylation, there are some ratios of complex oligosaccharides that are unique in the BCOC of the present invention even when considering all bovine and human oligosaccharides. Such unique BCOC oligosaccharide signatures include; 1) a ratio of Hex(2) NeuAc(1):Hex(2) HexNAc(1) less than 5.0; 2) a ratio of Hex(2) HexNAc(1):Hex (3) HexNAc(1) of greater than 1.0; 3) a ratio of Hex(2) HexNAc (1):Hex (3) HexNAc(2) of greater than 2.0; 4) a ratio of Hex(3):Hex (3) HexNAc(1) NeuAc(1) of less than 100; and 5) a ratio of Hex(2) HexNAc(1):Hex (4) NeuAc(2) NeuGc (1) of greater than 10 (Table 2).

TABLE 2

Ratios of specific oligosaccharides found in BCO, BCOC, BMO and HMO from Table 1

| Oligosaccharide ratios | BCO | BCOC | BMO | HMO |
|---|---|---|---|---|
| Hex(2) NeuAc(1):Hex (2) HexNAc(1) | 7.8 | 1.5 | 14.2 | 182.0 |

TABLE 2-continued

Ratios of specific oligosaccharides found in BCO, BCOC, BMO and HMO from Table 1

| Oligosaccharide ratios | BCO | BCOC | BMO | HMO |
|---|---|---|---|---|
| Hex(2) HexNAc(1):Hex (3) HexNAc(1) | 0.6 | 2.5 | 0.2 | 0.0 |
| Hex(2) HexNAc(1):Hex (30 HexNAc(2) | 0.6 | 1710.0 | 0.6 | 1.0 |
| Hex(3):Hex (3) HexNAc(1) NeuAc(1) | 227.0 | 17.5 | 1870.0 | 148.0 |
| Hex(2) HexNAc(1):Hex(4) NeuAc(2) neuGc(1) | 1.0 | 1710.0 | 6.1 | 1.0 |
| Hex(3):Hex(3) NeuAc(1) | 0.5 | 7.1 | 0.8 | 148.0 |
| Hex(3):Hex(4) HexNAc(2) | 227.0 | 5.0 | 36.0 | 3.6 |
| Hex(2) HexNAc(1):Hex(4) | 26.2 | 12.2 | 159.0 | 1.0 |
| Fucosylated oligosaccharides (% of total) | 0.00 | 0.00 | 0.00 | 0.00 |

This example demonstrates that HMO, BMO, BCO, and BCOC have distinctly different compositions. However, all four of these mixtures are able to activate *B. infantis*.

Example 4. Preparation of an Activated Bifidobacteria (ABI) Composition that can Exclusively Use Certain Complex Oligosaccharides Bifidobacteria *longum* subsp. *infantis* (alternatively *B. infantis* herein) was isolated and purified from the feces of a vaginally delivered, breast fed human infant and its identification was confirmed by DNA analysis that reflected the presence of a gene set that is specifically associated with this organism (Sela et al., 2008, *PNAS*, 105(48): p. 18964-69). Alternatively, a strain of *B. infantis* can be obtained from a commercial culture collection such as the American Type Culture Collection (ATCC) of Washington, D.C.

A seed culture of this organism was added to a growth medium comprising glucose and a BCO composition, made using the process described in Example 2, and other standard salts and vitamins in a 500 L agitated fermenter. Following 3 days of growth under anaerobic conditions, a sample of the culture was tested for the presence of ABI. ABI was identified by the presence of expressed gene transcripts for fucosidase or sialidase. The fermenter was harvested by centrifugation and the concentrated cell mass was mixed with a cryopreservative (e.g., trehalose plus milk proteins) and freeze dried. The final dry product was 5.5 kg of bacterial mass with a count of $130\times10^9$ cfu/g.

This example demonstrates that bifidobacteria can be activated by culturing the bifidobacteria with a complex bovine milk oligosaccharide. While BCO was used herein, this method or a similar method can be used to obtain ABI by culturing with MMO from any mammalian milk. Such ABI would be suitable for use in embodiments of this invention.

Example 5. Bifidobacteria Grown on Complex Oligosaccharides is Activated for Consumption of Milk Oligosaccharides

*B. infantis* ATCC 15697 was grown in MRS broth containing 2% lactose or bovine milk oligosaccharides (BMO). Cells were collected at exponential phase, RNA was purified and converted to cDNA and sequenced on an Illumina platform. Results clearly show differential expression during growth on BMO.

FIG. 1 depicts whole genome expression analysis. The diagram shows principle component analysis of all expressed genes within *B. infantis*. The diagram clearly shows differential expression of cells grown on BMO versus cells grown on lactose. 577 genes are differentially expressed suggesting growth on milk oligosaccharides induces a different physiological state in *B. infantis* than lactose.

Figure 2:
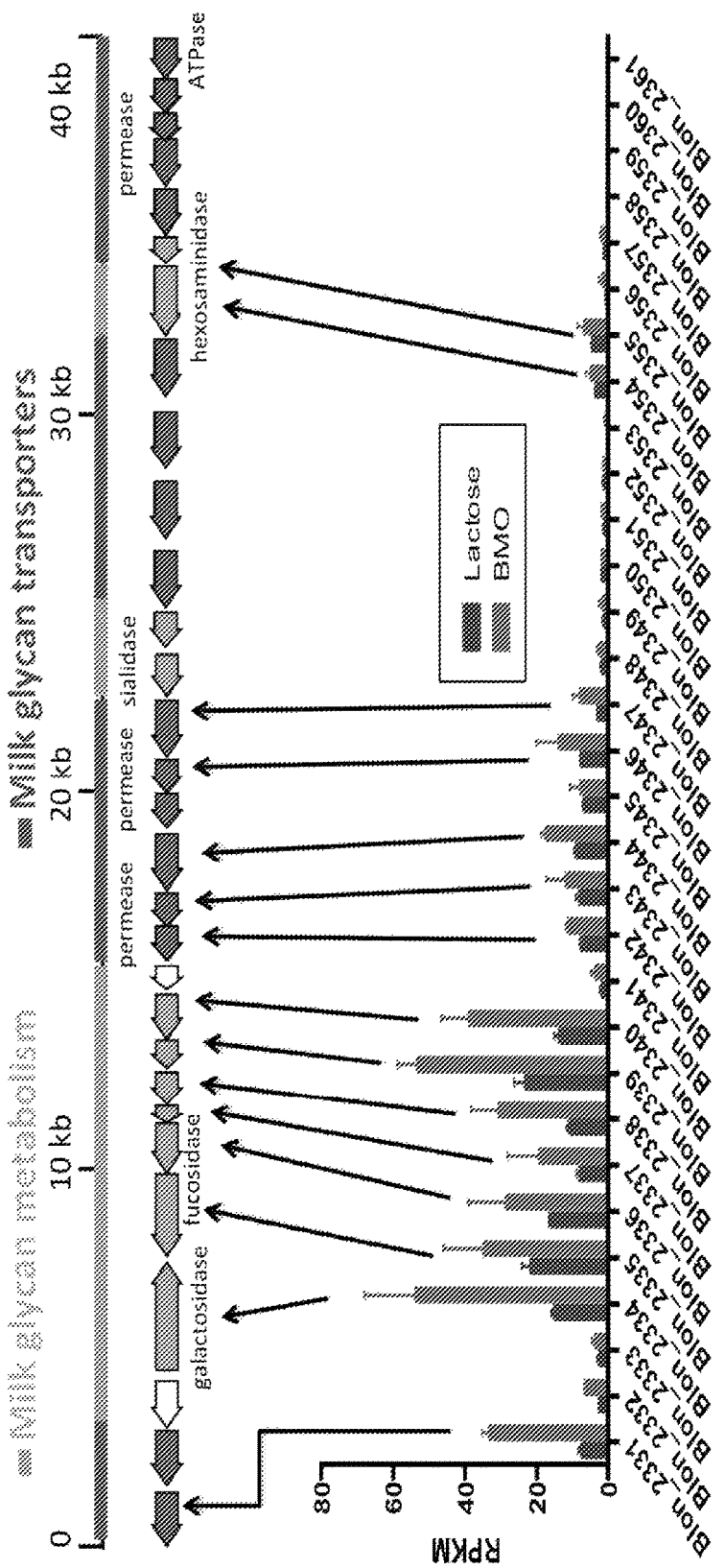
FIG. 2 is a diagram showing a selection of the genes of the milk oligosaccharide cluster differentially expressed in *B. infantis* during growth in the presence of bovine milk oligosaccharides (BMO) or lactose.

Further analysis shows that the 40 kb milk oligosaccharide consumption gene cluster previously identified in *B. infants* is preferentially induced during growth on BMO by comparison to growth on lactose as shown in FIG. 2. These results clearly show *B. infantis* grown on BMO is activated for consumption of milk oligosaccharide and a range of other genes involved in colonization and host interface in the neonate colon, including Blon_2334, Blon_2335, Blon_2336, Blon_2337, Blon_2338, Blon_2339, Blon_2344, Blon_2346, Blon_2347, and Blon_2331, are upregulated.

Example 6. Preparation of Therapeutic Compositions for the Treatment of Pregnant Women Preparation 1 is prepared by first diluting the ABI product of Example 4 with pharmaceutical grade lactose to provide a dose of 25 billion cfu of *B. longum* subsp. *infantis* per gram. This diluted ABI product is then packaged in 2-piece gel caps (1 g/gel cap) made of a gastric-resistant polymer such as pectin, to provide doses of 25 billion cfu of activated *B. longum* subsp. *infantis* per capsule in a delivery form that releases its contents in the GI tract beyond the stomach.

Preparation 2 is prepared by blending the ABI product of Example 4 with the BMO/SPF composition of Example 2 whereby 25 billion cfu of *B. longum* subsp. *infantis* (170 mg of the dry product) is blended with 5 g of the BMO/SPF composition of Example 2. Preparation 2 provides a ratio of 25 billion cfu of *B. longum* subsp. *infantis* to about 2.5 g BCO/SPF and this mixture is packaged in sachets made using a moisture and oxygen impermeable polymer.

Example 7. Administering Composition to Pregnant Women

The composition of Preparation 1 of Example 6 (ABI) is produced and the product is packaged in 2-piece gel caps (1 g/gel cap) made of a gastric-resistant polymer such as pectin, to provide doses of 25 billion cfu of *B. longum* subsp. *infantis* per capsule. A second preparation is made using the dry product of Preparation 2 of Example 6 and the product is packaged in sachets made using a moisture and oxygen impermeable polymer to provide a dose of 25 billion cfu of *B. longum* subsp. *infantis* plus 2 g BMO/SPF (5 g of the BMO/SPF composition of Example 2) per sachet.

The compositions described herein are taken orally by a woman throughout pregnancy but at least in the third trimester of pregnancy. For the initial treatment, a pregnant woman is provided with two capsules of Preparation 1, as described in Example 6, on a daily basis for the first 2 weeks of treatment. This process establishes the population of *B. longum* subsp. *infantis* in the gut of the woman. For subsequent weeks of treatment, the woman with is provided with 4 sachets per day of Preparation 2 of Example 6 to maintain the population of *B. longum* subsp. *infantis* at high levels in her gastrointestinal tract. The 4 sachets are taken throughout the day, one at each meal and one before going to bed. The contents of the sachet can be mixed with milk, yogurt or pudding to aid in oral consumption. If the levels of *B. longum* subsp. *infantis* fall below 25% of the levels established by the end of the 2-week pre-treatment with Preparation 1 of Example 6 as determined by fecal microbiome analyses, the patient is returned to the Preparation 2 treatments for an additional 2 weeks. Compositions of this invention according to alternative embodiments may be administered similarly. Administration should continue until the birth of the child. The treatment leads to a much higher likelihood that a vaginally-delivered infant will be appropriately inoculated with the *B. longum* subsp. *infantis* from the mother.

Example 8. Use of a Composition Comprising Bifidobacteria with an Expressed Fucosidase to Improve the Health of an Infant The final dry product of Example 4 (Activated *Bifidobacterium longum* subsp. *infantis*—at a bacterial count $130\times10^9$ cfu/g) is blended with pharmaceutical grade lactose to reach a bacterial count of about $25\times10^9$ cfu/g, and packaged into sachets made from moisture and oxygen resistant materials at a mass of 500 mg ($12.5\times10^9$ cfu) per sachet. The contents of one sachet is provided to a newborn infant who is exclusively receiving breast milk every day for a period of 6 months. The package is opened and the contents emptied into a small cup to which a few drops of breast milk is added to make a watery paste. This is then provided to the baby either using a blunt-tipped plastic dropper or the parent's fingertip. Best results are obtained if the baby consumes at least 75% of the daily composition each day. Monitoring of the infant fecal microbiota will indicate that the level of *B. infantis* in the feces will represent more than 20% of the total microbial load of the feces. This composition should be provided to all babies whether they are vaginally delivered, but especially if they are delivered by Caesarian Section.

Some mothers who are nursing their babies, may be deficient in certain complex fucosylated oligosaccharides in their milk because of a deficiency in al-2-fucoslyltransferase enzyme (FUC-2) as measured by a genetic test. For mothers who are of the genotype FUC-2, the sachet containing the ABI product of example 4 should be supplemented with a BCO composition containing synthetically produced and purified fucosylated oligosaccharides (SPF) at a BCO:SPF ratio of about 2:1 as described in Example 2. These sachets are prepared to deliver of $12.5 \times 10^9$ cfu of ABI and 1 g BCO plus 0.5 g fucosyllactose per sachet (i.e., 100 mg of the undiluted ABI of Example 4 plus 2.5 g of BCO of Example 2 plus 0.5 g of fucosyllactose per sachet). This composition is provided on a daily basis for 6 months as described above for the sachets of ABI alone.

For infants that are receiving mixed feeds (breast milk and infant formula) or exclusively infant formula, the ABI product of Example 4 is blended with a bovine colostrum oligosaccharide concentrate composition of Example 2. A composition of dried bovine colostrum oligosaccharide containing about 40% lactose and about 40% complex oligosaccharides (BCO) is prepared according to Example 2 and packaged in a moisture resistant sachet at a dose of 5 g/sachet (i.e., 2 g BCO/sachet)—the BMO sachet. Additional sachets containing a blend of the ABI product of Example 4 resulting in the delivery of $12.5 \times 10^9$ cfu of ABI, and 2 g BCO per sachet (ca. 100 mg of the undiluted ABI of Example 4 plus 5 g of BCO of Example 2)—the BLEND sachet. The contents of one BLEND sachet is provided to a baby on a daily basis who is otherwise receiving mixed feeds or exclusively receiving infant formula, by opening the sachet and dissolving its contents into the prepared liquid infant formula and providing it to the baby in a morning feed. Twelve hours later the process is repeated but with the BMO sachet (no ABI) delivered with the infant formula as described for the BLEND sachet. This daily cycle is repeated (BLEND in the morning, BMO in the evening) for at least the first 6 months of life. Monitoring of the infant fecal microbiota will indicate that the level of B. infantis in the feces will represent more than 20% of the total microbial load of the feces. This routine should be maintained for all babies whether they are vaginally delivered, or delivered by Caesarian Section, as long as they are not being exclusively breast-fed. Alternatively, the infant can be provided just the BLEND sachets twice per day providing the BLEND sachets are prepared with only $6 \times 10^9$ cfu of ABI per sachet.

These dietary supplements will increase the concentration of B. longum subsp. infantis in the lower bowel of the baby to those levels historically seen in vaginally-delivered, breast-fed babies, and will significantly reduce the likelihood of a pathogenic bacterial bloom that may cause colic in that baby. This supplementation will also significantly improve the rate of development of that baby's gastrointestinal mucosa and mucosal immune response. Compositions of this invention according to alternative embodiments may be administered similarly.

REFERENCES

Aldredge D L, Geronimo M R, Hua S, Nwosu C C, Lebrilla C B, Barile D. (2013) Annotation and structural elucidation of bovine milk oligosaccharides and determination of novel fucosylated structures. *Glycobiology*, 23 (6): 664-76.

Christiansen, S. et al. (2010). Chemical composition and nutrient profile of low molecular weight fraction of bovine colostrum. *International Dairy Journal*, 20: p. 630-36.

Garrido, D. S. Ruiz-Moyano, D. G. Lemay, D. A. Sela, J B. German and D. A Mills. (2015). Comparative transcriptomics reveals key differences in the response to milk oligosaccharides of infant gut-associated bifidobacteria. *Nature Scientific Reports* (In Press).

Huda, M N., Z. Lewis, K. Kalanetra, M. Rashid, S. Ahmad, R. Raqib, F. Qadri, M. A. Underwood, D. A. Mills and C. Stephensen. (2014). Stool microbiota and vaccine responses of infants. *Pediatrics,* 134:2 e362-e372.

Kim, J.-H., H. J. An, D. A. Garrido, J. B. German, C. B. Lebrilla and D. A. Mills. (2013). Proteomic analysis of *Bifidobacterium longum* subsp. *infantis* reveals the metabolic insight on consumption of prebiotics and host glycans. *PLoS ONE,* 8(2): e57535.

Le Pare et al. (2014). Rapid quantification of functional carbohydrates in food products. *Food and Nutrition Sciences,* 5: p. 71-78.

Lewis, Z. T., S. M. Totten, J. T. Smilowitz, M. Popovic, E. Parker, D. G. Lemay, M. L. Van Tassell, M. J. Miller, Y. S. Jin, J. B. German, C. B. Lebrilla and D. A. Mills. 2015. Maternal fucosyltransferase 2 status impacts gut bifidobacterial communities of breastfed infants. *Microbiome*, 3:13.

Mehra R, Barile D, Marotta M, Lebrilla C B, Chu C, German J B. (2014) Novel high-molecular weight fucosylated milk oligosaccharides identified in dairy streams. *PLoS One*, 9(5): e96040.

Sela et al. (2008). The Genome Sequence of *Bifidobacterium Longum* Subsp. *Infantis* reveals adaptations for milk utilization within the infant microbiome. *PNAS,* 105(48): p. 18964-69.

Sela D A and D A Mills (2010) Nursing our microbiota: molecular linkages between bifidobacteria and milk oligosaccharides. *Trends in Micorbiol* 18: 298-307.

Tao N, et al. (2009). Variations in bovine oligosaccharide during early and middle lactation stages analyzed by high-performance liquid chromatography-chip/mass spectrometry. *J Dairy Sci* 92: 2991-3001.

Underwood, M A, J B German, C B Lebrilla, and D A Mills (2015). *Bifidobacterium longum* subsp. *infantis*: champion colonizer of the human gut. *Pediatr Res,* 77: 229-235

Ward R E (2009). Isolation of milk oligosaccharides using solid phase extraction. *Open Glyceroscience* 2: 9-15.

Zivkovic A M, Barile D. (2011) Bovine milk as a source of functional oligosaccharides for improving human health. *Adv Nutr,* 2(3):284-9.

The invention claimed is:

1. A method of improving the health of a mammalian gastrointestinal tract comprising administering a therapeutically effective amount of a composition comprising activated *Bifidobacterium* to a subject in need thereof, wherein activated *Bifidobacterium* is *Bifidobacterium longum* subsp. *infantis* in which genes Blon_0042, Blon_2331, Blon_2337, Blon_2338, Blon_2339, and/or Blon_2346 are up-regulated.

2. The method of claim 1, wherein the activated *Bifidobacterium* contains a transport system capable of internalizing one or more oligosaccharide before said oligosaccharide is hydrolyzed and is further capable of hydrolyzing said internalized oligosaccharide, wherein said oligosaccharide has the structure of an oligosaccharide found in a mammalian milk.

3. The method of claim 1, wherein the activated *Bifidobacterium* has been cultured in the presence of at least one mammalian milk oligosaccharide.

4. The method of claim 1, wherein the activated *Bifidobacterium* has a higher binding affinity to mammalian mucosal cells than *Bifidobacterium* of the same species cultivated in the absence of complex oligosaccharides.

5. The method of claim 1, wherein the *Bifidobacterium* expresses a gene coding for a sialidase, a fucosidase, a sialic acid transporter, and/or a fucose transporter.

6. The method of claim 1, wherein the *Bifidobacterium* is present in the composition at a concentration of from 1 billion cfu/g to 500 billion cfu/g.

7. The method of claim 1, wherein the composition further comprises an isolated complex oligosaccharide.

8. The method of claim 1, wherein the composition further comprises a stabilizer.

9. The method of claim 1, wherein the composition is in the form of a dry powder, a dry powder suspended in an oil, or as a solution.

10. The composition of claim 1, wherein the composition is in the form of a packet, sachet, orally disintegrating tablet, foodstuff, capsule, lozenge, effervescent tablet, suppository, or enema.

11. A method of increasing the concentration of *Bifidobacterium* in the gastrointestinal tract of a mammal comprising administering an effective amount of a composition comprising activated *Bifidobacterium* to a mammal whereby levels of said administered *Bifidobacterium* in the feces of said mammal are increased to greater than 10% of the total microbiome found in that feces, wherein activated *Bifidobacterium* is *Bifidobacterium longum* subsp. *infantis* in which genes Blon_0042, Blon_2331, Blon_2337, Blon_2338, Blon_2339, and/or Blon_2346 are up-regulated.

12. The method of claim 11, wherein the activated *Bifidobacterium* contains a transport system capable of internalizing one or more oligosaccharide before said oligosaccharide is hydrolyzed and is further capable of hydrolyzing said internalized oligosaccharide, wherein said oligosaccharide has the structure of an oligosaccharide found in a mammalian milk.

13. The method of claim 11, wherein the activated *Bifidobacterium* has been cultured in the presence of at least one mammalian milk oligosaccharide.

14. The method of claim 11, wherein the activated *Bifidobacterium* has a higher binding affinity to mammalian mucosal cells than *Bifidobacterium* of the same species cultivated in the absence of complex oligosaccharides.

15. The method of claim 11, wherein the *Bifidobacterium* expresses a gene coding for a sialidase, a fucosidase, a sialic acid transporter, and/or a fucose transporter.

16. The method of claim 11, wherein the *Bifidobacterium* is present in the composition at a concentration of from 1 billion cfu/g to 500 billion cfu/g.

17. The method of claim 11, wherein the composition further comprises an isolated complex oligosaccharide.

18. The method of claim 11, wherein the composition further comprises a stabilizer.

19. The method of claim 11, wherein the composition is in the form of a dry powder, a dry powder suspended in an oil, or as a solution.

20. The method of claim 11, wherein the composition is in the form of a packet, sachet, orally disintegrating tablet, foodstuff, capsule, lozenge, effervescent tablet, suppository, or enema.

21. The method of claim 1, wherein the subject is a human infant.

22. The method of claim 11, wherein the mammal is a human infant.

* * * * *